US012631647B2

(12) United States Patent
Xia et al.

(10) Patent No.: US 12,631,647 B2
(45) Date of Patent: May 19, 2026

(54) LOCK AND KEY TEMPLATION OF MOLECULARLY IMPRINTED POLYMER FOR SMALL MOLECULE RECOGNITION

(71) Applicant: PALO ALTO RESEARCH CENTER INCORPORATED, Palo Alto, CA (US)

(72) Inventors: Kelly Xia, Berkeley, CA (US); Stephen Matthew Meckler, Campbell, CA (US); Gabriel Iftime, Newark, CA (US); Mahati Chintapalli, Mountain View, CA (US); Jerome Unidad, Paris (FR)

(73) Assignee: GENESEE VALLEY INNOVATIONS, LLC, Santa Clara, CA (US)

( * ) Notice: Subject to any disclaimer, the term of this patent is extended or adjusted under 35 U.S.C. 154(b) by 960 days.

(21) Appl. No.: 17/880,398

(22) Filed: Aug. 3, 2022

(65) Prior Publication Data

US 2024/0044905 A1 Feb. 8, 2024

(51) Int. Cl.
| | |
|---|---|
| *G01N 33/58* | (2006.01) |
| *C08F 220/06* | (2006.01) |
| *G01N 21/64* | (2006.01) |
| *G01N 33/94* | (2006.01) |

(52) U.S. Cl.
CPC ........... *G01N 33/58* (2013.01); *C08F 220/06* (2013.01); *G01N 21/6428* (2013.01); *G01N 33/94* (2013.01); *G01N 2021/6439* (2013.01); *G01N 2600/00* (2013.01)

(58) Field of Classification Search
CPC .... G01N 33/58; G01N 33/94; G01N 21/6428; G01N 2021/6439; G01N 2600/00; C08F 220/06
See application file for complete search history.

(56) References Cited

U.S. PATENT DOCUMENTS

| | | | | |
|---|---|---|---|---|
| 11,493,451 | B2 * | 11/2022 | Iftime | ..................... G01N 31/22 |
| 2018/0214845 | A1 * | 8/2018 | Gluckman | .............. C02F 1/285 |
| 2020/0255202 | A1 * | 8/2020 | Steele | ................ B65D 75/5866 |

OTHER PUBLICATIONS

Alonzo et al., Portable testing techniques for analysis of drug materials, Apr. 4, 2022, WIREs Forensic Science Wiley, pp. 1-18. (Year: 2022).*

* cited by examiner

*Primary Examiner* — Kathryn Elizabeth Limbaugh
(74) *Attorney, Agent, or Firm* — Miller Nash LLP

(57) ABSTRACT

A composition of matter has a molecularly imprinted polymer having templated pores, and a reactive material occupying a portion of each pore, the reactive material selected to react when an analyte material for which the cavities are templated enters the cavities. A method of synthesizing a molecularly imprinted polymer includes arranging monomers around a template molecule having a reactive component and an analyte component, polymerizing the monomers, removing the template molecule, and reintroducing the reactive component of the template molecule. A method of detecting an analyte includes exposing a molecularly imprinted polymer to a fluid, the polymer having templated pores containing a detector material that is reactive to an analyte.

20 Claims, 3 Drawing Sheets

LOCK AND KEY TEMPLATION OF MOLECULARLY IMPRINTED POLYMER FOR SMALL MOLECULE RECOGNITION

TECHNICAL FIELD

This disclosure relates to rapid screening tests, more particularly to using small molecule dyes.

BACKGROUND

Current screening methods for rapid sensing and detection can be improved by decreasing the time required to complete a test, decreasing the cost of testing, and improving the accuracy and sensitivity of testing. Rapid detection of different compounds has several application, including affordable, low cost and rapid screening for drugs, whether legal or illegal, from fluids such as saliva, urine and blood. For example, first responders need to be able to quickly detect the presence of extremely dangerous drugs such as fentanyl, before being exposed. There is also a need for a rapid test to detect accidental ingestion of toxic chemicals, in order to speed up patient treatment. In addition, most illnesses are associated with evolution of specific metabolites. A low-cost screening method would enable more frequent monitoring for early detection of these sicknesses. Another need relates to health monitoring. For example, glucose testing is done quite often at home. The cost of glucose test strips of the current devices is very high. For this reason, many patients may not perform as many tests as needed to maintain healthy glucose levels. A test method that has a significantly lower cost will increase the testing frequency, enabling patients to take action faster, before side effects of high glucose come into effect.

SUMMARY

According to aspects illustrated here, there is provided a composition of matter having a molecularly imprinted polymer having templated pores, and a reactive material occupying a portion of each pore, the reactive material selected to react when an analyte material for which the cavities are templated enters the cavities.

According to aspects illustrated here, there is provided a method of synthesizing a molecularly imprinted polymer including arranging monomers around a template molecule having a reactive component and an analyte component, polymerizing the monomers, removing the template molecule, and reintroducing the reactive component of the template molecule.

According to aspects illustrated here, there is provided a method of detecting an analyte including exposing a molecularly imprinted polymer to a fluid, the polymer having templated pores containing a detector material that is reactive to an analyte.

DETAILED DESCRIPTION OF THE EMBODIMENTS

The embodiments here involve a method to decouple chemical functionality from substrate selectivity using small molecules. In many cases, increasing a system's selectivity for specific substrates, analytes, or reactivity can greatly drive up its cost. Selectivity is often implemented through complicated chemical structure modifications, which makes bulk material synthesis impractically expensive. The embodiments have the potential to create a highly selective platform using inexpensive commercial chemical feedstocks by exploiting thermodynamically favorable self-organization effects in material synthesis. The process by which selectivity is enforced is independent of the material's functional component or "active site." This decoupling allows functionality and selectivity to be optimized without co-dependence, which may lower the overall cost greatly and provide advantages in a wide range of chemical applications.

While much of the discussion below focuses on detection of materials, such as drugs and other chemical compounds, the embodiments may involve sensing of different materials. As used here, the term "sensor" means a device that measures quantities of some condition or amount, such as temperature. The term "detector" means a device that determines the presence of something and is a type of sensor. Detection does not necessarily apply to sensing, for example, because a sensor could detect light levels and light will generally always be present.

Generally, molecularly imprinted polymers (MIPs) result from templating monomers around a molecule of interest, then polymerizing the monomers. This creates a cavity structurally tailored to the molecule of interest. Referring to the top of FIG. 1, the monomers 10 assemble around the molecule of interest, referred to here as the template molecule 12. The monomers assemble in a self-organizing manner through various non-covalent or reversibly covalent interactions, such as hydrogen bonding, dipole interactions, and hydrophobic/hydrophilic effects.

Once the monomers have assembled, they undergo polymerization to form polymer 14, preserving their spatial orientation. The template molecule 12 is then removed, leaving cavities, or pores, 16. These cavities 16 can selectively recognize and bind the template molecule when it is reintroduced. Their structural orientation is tailored to have especially favorable interactions with the template molecule through both steric and electronic effects. MIPs act most effectively with "small" molecule. As used here, the term "small molecule" means a molecule having low molecular weight, and typically around 1 nanometers in size.

Figure 1:
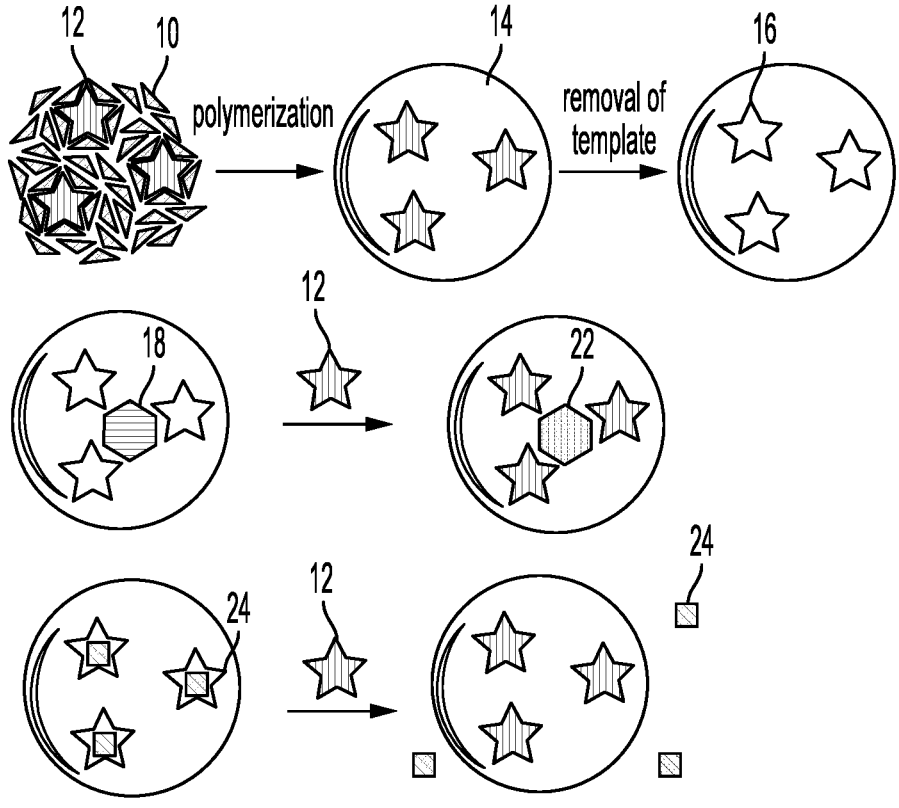
FIG. 1 shows a graphical representation of conventional synthesis of a molecularly imprinted polymer.

For most sensing devices, simple recognition of the template molecule, which may comprise an analyte, in the MIP must be paired with another reactive and detectable mechanism. In some cases, the analyte can induce a change in fluorescence emission or color through interactions with the MIP. The middle of FIG. 1 shows a detection mechanism. The template cavities from the top process have a detection material 18. When the MIP comes into contact with the analyte, or template molecule, 12, the detection material 18 changes to look like 22. An example of such an occurrence involves an MIP synthesized around a graphene quantum dot (GQD). The GQD is functionalized with vinyl groups, allow it to incorporate into the center of the MIP. However, this method requires the design of a fluorescent compound that can integrated into the MIP or bind to the MIP, which may be challenging and limiting. Modifying a dye molecule to include a functional group that can integrate into the polymerization may greatly increase the cost of the material in some cases.

Alternatively, the process can use a dye molecule that binds weakly in the template cavity of the MIP. With introduction of the analyte, which binds more strongly in the cavity, the analyte displaces the dye molecule. The process can then detect the dye molecule in solution. The bottom of FIG. 1 shows this process. The dye molecule 24 having weak bonds resides in the cavity. When the MIP is exposed to the analyte 20, the analyte displaces the dye molecule 24 into solution. This process has challenges for small molecules, as the dye must be smaller than the analyte and have structural similarities. Either of the detection processes of FIG. 1 impost severe limitations on the choice of a detector compound.

The embodiments here essentially decouple selectivity from sensitivity. First, a reactive compound, such as a derivatizing agent, is chosen to meet the desired testing conditions, such as it binds to the analyte quickly, the derivatized analyte is detectable at the desired low concentrations to satisfy sensitivity requirements, etc. Next, an MIP is synthesized to increase selectivity for the analyte of interest. This method should, in theory, broaden the scope of viable detection compounds and methods, allowing the selection of an optimally sensitive and fast method without consideration for selectivity. Then, selectivity and specificity for the analyte can be achieved by tailoring an MIP to the selected detection method.

This strategy can also be applied to a number of other applications in which selectivity and cost-reduction are important. For example, separation and purification processes for small molecules, and selective catalysis for the commercial synthesis of pharmaceutical compounds or other structurally complicated small molecules. In the separation case, a simple, cheap, and rapidly reversible binding agent can be chosen for the analyte of interest. The chosen binding agent can be indiscriminate in reactivity, as specificity can be enhanced by embedding the binding agent in an MIP-based membrane or sorbent based on our invention. In the catalysis case, a number of organic and organometallic catalysts can be embedded in an MIP, which can enforce selective control over either the substrate or reaction transition state, enabling potentially both rate acceleration and enhanced selectivity. By avoiding structural modifications of the catalyst, selectivity can be enhanced at a relatively low cost, and without affecting catalyst functionality. Structural modifications can often change the electronic properties and reactivity of a catalyst.

Figure 2:
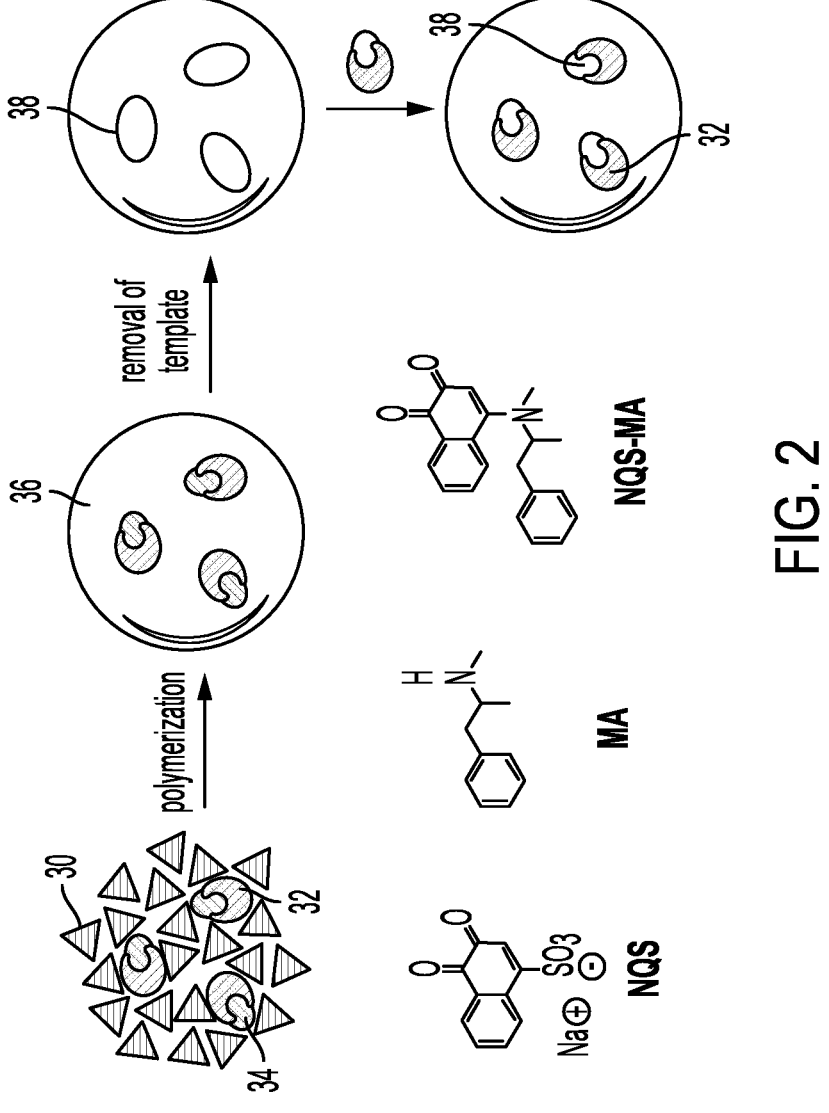
FIG. 2 shows graphical representation of an embodiment of synthesis of a molecularly imprinted polymer.

The embodiments here synthesize an MIP around a template molecule of an analyte material and a detector material. The process then removes the template compound molecule after polymerization. The process then reintroduces the detector component of the template molecule that occupies a fraction of the template cavity or pore. The remainder of the cavity is tailored to fit the analyte. This renders an otherwise unselective detector selective and specified to react with only the desired analyte. One could envision this as a "lock" and "key" mechanism, wherein the dye or other detector material acts as the lock and the analyte is the key. FIG. 2 shows a general diagram of the process and a more specific version.

In FIG. 2, the monomers 30 are arranged around the molecules of interest, comprising a detector material 32 and an analyte of interest 34. The arranging may comprise arranging the monomers with one of reversible covalent or non-covalent interactions and bind through one of either steric or electronic effects. The monomers undergo polymerization, such as by one of radical, condensation, or ring opening polymerization, resulting in the polymer 36 with the molecules of interest. The template is then removed, resulting in the template pores or cavities such as 38. The removal may comprise washing or extraction to remove the template molecule. The detection component 32 is then reintroduced into the cavities, leaving a portion of the cavity 38 tailored to fit the analyte of interest. The detector material may include functional groups reactive to the analyte.

As an example, shown in the lower portion of FIG. 2, the analyte of interest is methamphetamine (MA). The detector material in the example 1,2-naphthoquinone-4-sulfonate (NQS). NQS reacts rapidly with MA to form the composite molecule NQS-MA, which has enhanced fluorescent emission compared to NQS alone. The fluorescence enhancement is detectable at extremely low concentrations (15 ng/mL of MA). However, NQS does not react selectively with MA, and also give false positive detection for various cross contaminants that contains amines.

In the example, the inventors have synthesized an MIP templated by NQS-MA, using methacrylic acid monomers and ethylene glycol dimethacrylate as a cross-linker in chloroform as a solvent with AIBN as a radical initiator, after oxygen removal from the solution. The reaction was performed at 60 deg C. for 3 hours. The NQS-MA is removed from the polymer by Soxhlet extraction, and NQS alone is reintroduced as the "lock" component, forming MIP⊃NQS. The NQS occupies a cavity that is tailored to accommodate NQS-MA. When MA is introduced, it can fit in the empty "key" space of the cavity, but other cross contaminants, in theory, cannot. The MIP selectively recognizes MA, and NQS-MA. This MIP⊃NQS material should exhibit fluorescence enhancement with similar sensitivity and speed as the NQS system without the MIP, but with superior selectivity for MA.

Various sensing mechanisms and chemistries for creating the "lock" and key" sensing mechanisms may be used. First, the sensing mechanism may be achieved by fluorescence change, by color change (colorimetric), by optical transmission change and other means, including spectroscopic changes. Other fluorescent dyes may be used to react with methamphetamine for example. There are numerous commercially available dyes designed to react with amines for protein tagging, such as fluorescamine, fluorescein derivatives, dansyl derivatives, etc. Previously, these have been of little interest in MA detection, as they react indiscriminately with amines. In combination with the "lock and key" MIP, these dyes may become integrated in sensing devices.

In addition, other compounds with chemical structures similar to methamphetamine may be detected using the NQS or other fluorescent dyes. This includes for example 3,4-Methylenedioxy-methamphetamine (MDMA), ecstasy, 4-Methylenedioxy-N-ethylamphetamine (MDEA), ephedrine, pseudoephedrine and others. By using the methods from the present invention, a screening test specific for detection of any of the above compounds can be designed.

Figure 3:
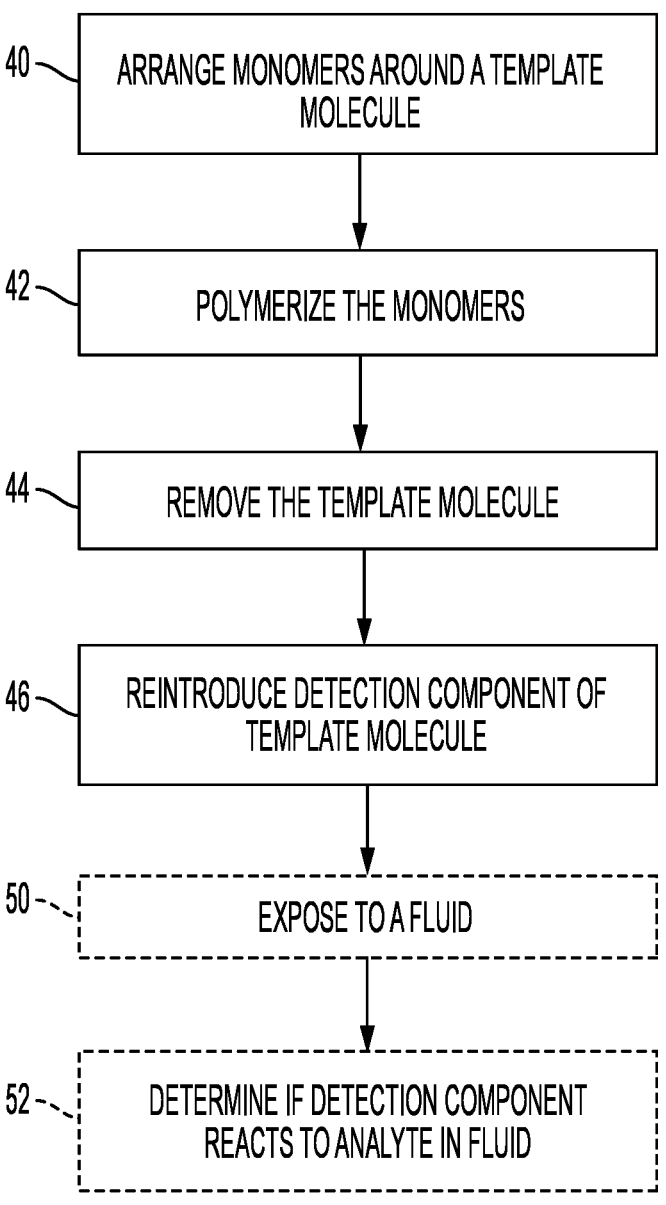
FIG. 3 shows a flowchart of a method for manufacturing a molecularly imprinted polymer.

FIG. 3 shows a general method of manufacturing the polymer with the templated cavity containing the detection component of the template molecule. At 40, the monomers are arranged around the template molecule that contains the detection material and the analyte of interest. The monomers are then polymerized around the template molecules at 42. The template molecule is then removed at 44, and the detection component is reintroduced to occupy a portion of the templated cavities.

Once the polymer with the detection material has been created, it can be used to screening. This may involve exposing the polymer to a fluid that may or may not contain the analyte of interest at 50. Depending upon the presence of the analyte of interest, the detection component reacts or not. The detection method may involve one of the reactions mentioned above and may result from separation of the analyte from the fluid, as discussed above regarding the prior art, using the MIP as a membrane.

In addition, a "lock and key" sensor can be created where the detection is based on color change and on different chemistries. For example, the Simon's reagent is widely used in solution for screening for methamphetamine and MDMA, but gives false positives to many secondary amine compounds including those exemplified above. Implementation of the present invention increases the selectivity for methamphetamine and MDMA. As another example, one preferred method for detection in solution of tetrahydrocannabinol (THC) is reaction with a specific dye such as Fast blue B dye (FBBS), which results in a color change. Compounds similar to THC which are legal, for example cannabidiol (CBD) is not a controlled substance and may give false positive results when tested in solution. In this specific case, first a "lock and key" compound is formed by a coupling reaction of the diazonium group from the FBBS dye with the phenyl group present on the THC molecules. The reaction is favored by the presence of the phenolic group (electron-donating) on THC. Then this compound is used for producing the MIP structure. Then FBBS (detector) is introduced in the MIP structure. This sensor can discriminate between THC, which can enter the MIP support, while other cross contaminants such as CBD are rejected, resulting in increased selectivity towards THC. It may also allow detection of the metabolites for THC based upon a position of the carboxylic acid group to determine if the person is under the influence of THC or had just used it recently.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent, or similar purpose, unless expressly stated otherwise.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art, which are also intended to be encompassed by the following claims.

What is claimed is:

1. A composition of matter, comprising:
a molecularly imprinted polymer having templated pores; and
a removable reactive material occupying a portion of each pore, the reactive material selected to react when an analyte material for which the pores are templated enters the pores.

2. The composition of matter as claimed in claim 1, wherein the reactive material has a characteristic that changes in a detectable manner in response to the analyte.

3. The composition of matter as claimed in claim 1, wherein the templated pores are configured to bind to at least one of the reactive material and the analyte material through one of either steric or electronic effects.

4. The composition of matter as claimed in claim 1, wherein the reactive material includes functional groups reactive to the analyte.

5. The composition of matter as claimed in claim 1, wherein the reactive material is a detector material.

6. The composition of matter as claimed in claim 5, wherein the detector material is 1,2-naphthoquinone-4-sulfonate (NQS), and the analyte is one of the group consisting of: methamphetamine, 3,4-Methylenedioxyl-methamphetamine (MDMA), 4-methylenedioxyl-N-ethyl-ampthetamine (MDEA) ephedrine, and pseudoephedrine.

7. The composition of matter as claimed in claim 5, wherein the detector material comprises Fast blue B dye and the analyte comprises tetrahydrocannabinol.

8. The composition of matter as claimed in claim 1, wherein the reactive material has a response that is at least one of colorimetric, fluorescent, optical transmission change, or a spectroscopic detectable change.

9. The composition of matter as claimed in claim 1, wherein the analyte is a small molecule.

10. A method of synthesizing a molecularly imprinted polymer, comprising:
arranging monomers around a template molecule having a reactive component and an analyte component;
polymerizing the monomers;
removing the template molecule; and
reintroducing the reactive component of the template molecule.

11. The method as claimed in claim 10, wherein arranging the monomers around a template molecule comprises arranging monomers with one of reversible covalent or reversible non-covalent interactions.

12. The method as claimed in claim 10, wherein polymerizing the monomers further comprises adding at least one of other monomers and cross-linkers prior to polymerizing the monomers.

13. The method as claimed in claim 10, wherein polymerizing the monomers comprises one of radical polymerization, condensation polymerization, and ring opening polymerization.

14. The method as claimed in claim 10, wherein removing the template molecule comprises at least one of washing and extraction.

15. The method as claimed in claim 10, further comprising washing the polymer after reintroducing the reactive component to remove any excess of the component.

16. The method as claimed in claim 10, wherein the template molecule has a first component as 1,2-naphthoquinone-4-sulfonate (NQS), and a second component as one of the group consisting of: methamphetamine, 3,4-Methylenedioxyl-methamphetamine (MDMA), 4-methylenedioxyl-N-ethylampthetamine (MDEA) ephedrine, and pseudoephedrine.

17. The method as claimed in claim 10, wherein the template molecule has a first component as Fast blue B dye and a second component as tetrahydrocannabinol.

18. A method of detecting an analyte comprising exposing a molecularly imprinted polymer to a fluid, the polymer having templated pores containing a detector material that is reactive to an analyte.

19. The method as claimed in claim 18, further comprising separating the analyte from the fluid using the molecularly imprinted polymer as a membrane.

20. The method as claimed in claim 18, wherein the detector material reacts to the analyte by one of a colorimetric, fluorescent, optical transmission, or spectroscopic change.

* * * * *